US007143050B2

(12) United States Patent
Crane

(10) Patent No.: US 7,143,050 B2
(45) Date of Patent: Nov. 28, 2006

(54) MEDICAL FACILITY BUILDING STRUCTURE

(76) Inventor: Harold E. Crane, P.O. Box 6169, Kingwood, TX (US) 77325-6169

( * ) Notice: Subject to any disclaimer, the term of this patent is extended or adjusted under 35 U.S.C. 154(b) by 855 days.

(21) Appl. No.: 10/309,274

(22) Filed: Dec. 4, 2002

(65) Prior Publication Data

US 2004/0111290 A1 Jun. 10, 2004

(51) Int. Cl.
*G06Q 10/00* (2006.01)
(52) U.S. Cl. .................. 705/2; 705/3; 340/286.07; 340/573.1
(58) Field of Classification Search ............. 705/2, 705/9, 29, 14, 3; 707/104.1; 342/463; 340/539.13, 340/573.4
See application file for complete search history.

(56) References Cited

U.S. PATENT DOCUMENTS

| | | | | |
|---|---|---|---|---|
| 5,732,401 | A * | 3/1998 | Conway | 705/29 |
| 5,748,907 | A * | 5/1998 | Crane | 705/2 |
| 6,283,761 | B1 * | 9/2001 | Joao | 434/236 |
| 6,529,164 | B1 * | 3/2003 | Carter | 342/463 |
| 2002/0165733 | A1 * | 11/2002 | Pulkkinen et al. | 705/2 |
| 2003/0046304 | A1 * | 3/2003 | Peskin et al. | 707/104.1 |

FOREIGN PATENT DOCUMENTS

CA 2307998 A1 * 11/2000

OTHER PUBLICATIONS

LastWord Enterprise Clinical SystemBrochure. IDX Systems Corporation publication. 2000. [Retrieved on May 15, 2003]. Retrieved from Internet. URL: <http://www.mindpop.com/pdf/IDXAmbulatory.pdf>.*
Tracker Locating Systems website. Oct. 18, 2000. [Retrieved on May 15, 2003]. Retrieved from Internet. URL: <http://web.archive.org/web/20001018122633/www.tracker.fi/tracker_30.html>.*

* cited by examiner

*Primary Examiner*—Joseph Thomas
*Assistant Examiner*—Natalie A. Pass
(74) *Attorney, Agent, or Firm*—Foley & Lardner LLP

(57) ABSTRACT

A method for directing a patient within a medical facility having a main corridor with an entrance at one end and an exit at another end, and with several hallways that extend substantially perpendicular off the main corridor. Each room in the medical facility has a room number, whereby the room numbers signify a relative location of each room with respect to the entrance and the exit and the other rooms in the medical facility. A patient enters the medical facility and goes to a receiving area near the entrance, and then is directed to go to a particular room number in the medical facility. If the patient is treated in different rooms, the patient knows where to go next after one treatments is finished, based solely on the room number of the next room as compared to the room number of the current room that the patient is in.

12 Claims, 2 Drawing Sheets

MEDICAL FACILITY BUILDING STRUCTURE

BACKGROUND OF THE INVENTION

A. Field of the Invention

The invention relates to a medical facility building structure that allows a patient to easily navigate his or her way through the facility.

B. Description of the Related Art

When a person goes to a medical facility, they typically have a difficult time finding the various rooms that they have to go to. For example, a person may be told to go to a waiting room, or to a doctor's room. The person may be told to go to a lab for blood samples. That person may then have to go to an office, in order to fill out papers, and after tests go to a check-out room, etc.

Needless to say, many persons get frustrated trying to get to the correct room in a medical facility. When a person checks in, the person is typically told to wait in a waiting room. After a period of time, that person is then checked by a doctor or by a nurse in a doctor's room. From there, the person may be sent to different rooms in order to have different tests performed. However, the person usually is given poor instructions as to where to go, and that person sometimes gets lost within the medical facility as a result.

Within the medical facility, a person may be given a variety of directions and instructions from different people along the route on how to get where the person has to go to. For example, the person may be told to "Follow signs for the cafeteria, and then turn left into a corridor, where you will find the X-ray room." Such cryptic directions are difficult to follow, needless to say.

Providing directions is a big problem, mainly because communicating with people is not always simple. Instructions and directions are given differently by different persons, and understanding them is another problem onto itself. In a large complex facility such as a medical facility, this problem is exacerbated. One may get directions from several different people on their way to a desired location within the facility, whereby those instructions may conflict with each other.

SUMMARY OF THE INVENTION

According to one aspect of the invention, there is provided a medical facility, which includes a main corridor that extends from an entrance to an exit of the medical facility. The medical facility also includes at least two dead-end hallways that extend substantially perpendicular from the main corridor. The at least two dead-end hallways each includes at least one room accessible therefrom. A sign is provided adjacent to each of the rooms, wherein rooms are given sequential numbers depending on their location with respect to the entrance.

According to another aspect of the invention, there is provided a method for directing patients to proper locations within a medical facility. The method includes providing at least one sign adjacent an entrance to the medical facility, which directs a patient to a counter. The method also includes determining, based on real-time information as to locations of medical facility staff, whether or not the patient can be treated by one of the medical facility staff. The method further includes, if it is determined that the patient can be treated immediately, providing the patient with an electronic card so as to monitor a current location of the patient, and directing the patient to a room within the medical facility. The medical facility includes a plurality of rooms which are provided either on a main corridor that extends from the entrance to an exit of the medical facility, or along at least two dead-end hallways that extend perpendicular from the main corridor.

BRIEF DESCRIPTION OF THE DRAWINGS

The foregoing advantages and features of the invention will become apparent upon reference to the following detailed description and the accompanying drawings, of which.

DETAILED DESCRIPTION OF SPECIFIC EMBODIMENTS

Preferred embodiments of the invention will be described in detail with reference to the drawings. The present invention is directed to a building floor plan for a medical facility, which allows a patient to easily find their way between rooms in the facility.

As explained previously, most medical facilities have complex floor plans, whereby it is difficult for a patient to navigate his or her way between different rooms, such as going from an X-ray examination room to an Upper-GI examination room. This is especially true in the case where a person seeking directions is not feeling well, which is typically the case for most persons who are seeking care in a medical facility.

The present invention can be utilized for any type of medical facility, such as, for example, a medical facility that provides automated interactive dynamic real-time management services as described in U.S. Pat. No. 5,748,907, which is issued to the same inventor as this application, and which is incorporated in its entirety herein by reference. In the '907 patent, a person's location is monitored within a medical facility, using electronic cards, for example, and that information provided to a computer network within the medical facility. With this information, the location of important personnel, such as a surgeon, can be determined quickly and accurately.

Figure 1:
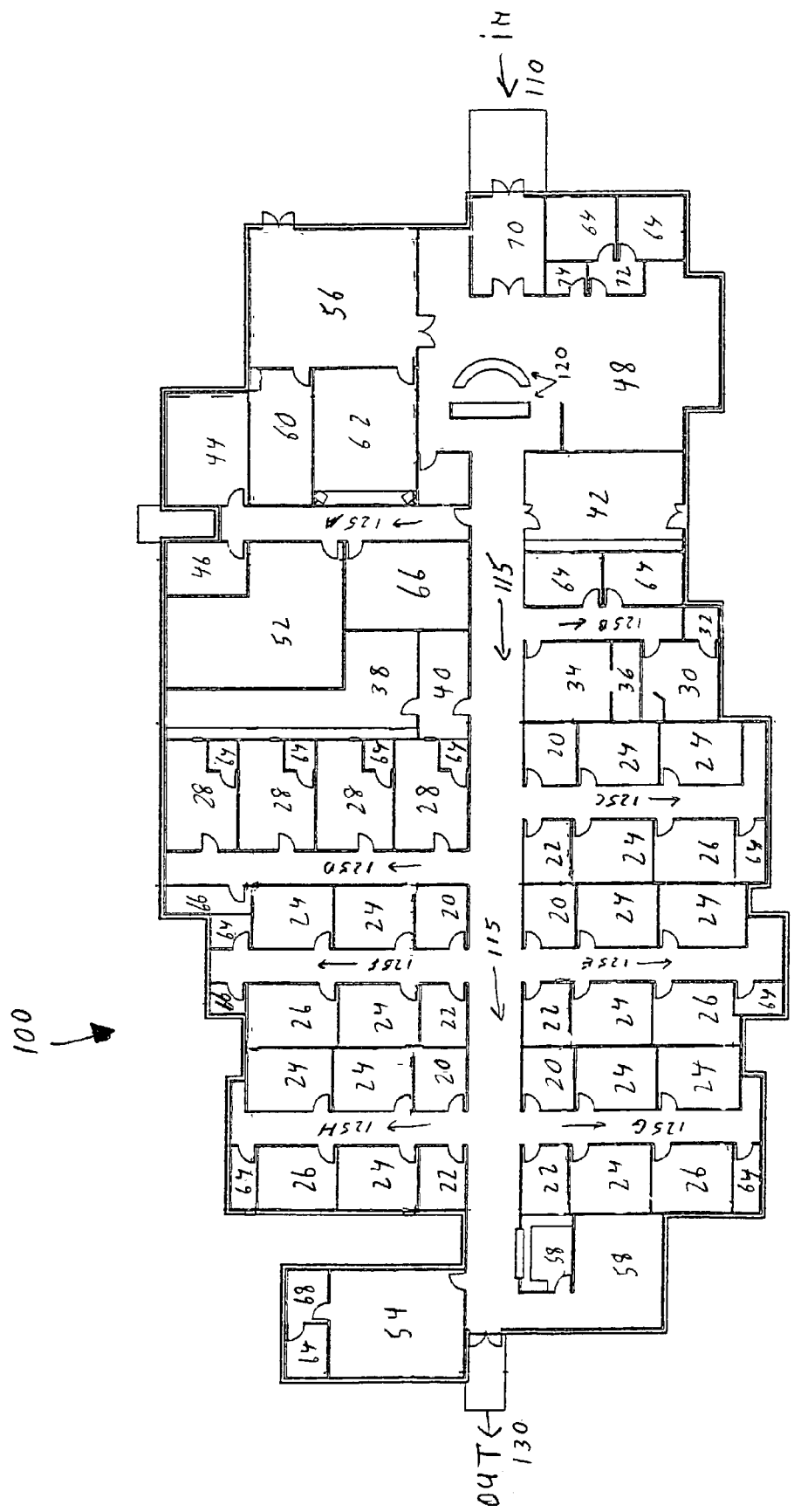
FIG. 1 is a floor plan that may be utilized by a medical facility in accordance with a first embodiment of the invention.

FIG. 1 shows a floor plan of a medical facility building structure 100 that may be utilized in accordance with a first embodiment of the invention, in order to allow a patient to easily navigate his or her way between rooms of the facility. A patient enters the medical facility 100 via a front entrance 110, whereby the first thing that the patient encounters is a large counter 120 facing the front entrance 110. The counter 120 is manned by one or more employees of the medical facility 100.

In the present invention, the patient is directed to first go to the counter 120, by way of a sign that is prominently displayed nearby the counter 120. For example, the sign may have "All Patients Must First Check In Here" or something to that effect written in big letters thereon. At the counter 120, the patient is provided with an electronic card, which is preferably the size of a credit card. The patient's name and other pertinent information (e.g., insurance information, brief description of reason for visit, etc.) is obtained by a person manning the counter 120, and is read into the electronic card prior to being given to the patient.

The patient is told to clip the electronic card onto his or her clothing. The electronic card is used in order to track the location of the patient when the patient is in the medical facility 100, as described in detail in the '907 patent. When the patient enters a room in the medical facility 100, information stored onto the patient's electronic card is scanned and read, and that information is provided to a computer network within the medical facility 100 in order to track in real time the current location of the patient and all other patients within the medical facility 100. Also, all employees of the medical facility 100, such as doctors, nurses, janitors, Information Technology personnel, etc., have electronic cards so that their current locations can be tracked in real time.

In the system and method described in the '907 patent, a medical facility employee at the counter 120 is provided with information on his or her computer screen regarding the location of all persons within the medical facility 100. That way, a patient can be routed to a room where a doctor is located and where no patients are currently located, in order that a patient at the counter 120 can be sent there to be treated quickly and effectively. As explained in detail in the '907 patent, data from each electronic card worn (or otherwise held) by patients and medical facility employees is entered into a computer network. Each electronic card has a unique identification (ID) code for tracking each person within the medical facility 100. Each room within the medical facility 100 has a capacity to scan electronic cards (e.g., card scanner, electro-optical device, etc.), so that information as to all persons within each room of the medical facility 100 is continuously updated and provided to a computer network within the medical facility 100. Thus, if Doctor Smith is currently in Room #4, as determined by an electronic card worn by Doctor Smith that has been scanned by a scanning device within Room #4, that information is provided to a computer accessible by a medical facility employee at the counter 120. That way, it can be determined whether or not a new patient who just came to the counter 120 should be directed to Doctor Smith in Room #4 (such as the case where there is no patient currently in Room #4).

In a preferred implementation of the first embodiment of this invention, the medical facility 100 is a one-story facility with a long main corridor 115. A front entrance 110 for the medical facility 100 is provided at one end of the main corridor 115, and a back exit 130 at an opposite end of the medical facility 100. With such a construction, each patient makes his or her way from entrance 110 to exit 130, along the main corridor 115, which lessens the chances of the patient getting lost trying to get to a particular room within the medical facility 100.

In the first embodiment, the counter 120 is provided about 15 feet or so inside the main corridor 115 (of course, other distances may be contemplated, while remaining within the scope of the invention). As explained above, the counter 120 is manned by medical facility personnel to guide a patient to the proper initial location (or room) within the medical facility 100. In the first embodiment, the rooms within the medical facility 100 are either entered via a door on a wall of the main corridor 115, or entered via a door on a wall of one of the short dead-end hallways 125A to 125H that extend perpendicularly to either the left or the right of the main corridor 115. With such a building structure, a patient is directed by a medical facility employee at the counter 120 to walk down the main corridor 115, and to go to a particular room number by way of a door that is either on the corridor 115 or on one of the short dead-end hallways 125A to 125H that jut off of the main corridor 115. In a preferred implementation, the main corridor 115 is 90 to 100 yards long, and each of the short dead-end hallways 125A to 125H is 10 to 20 yards long. Of course, other lengths may be envisioned while remaining within the scope of the invention.

Figure 2:
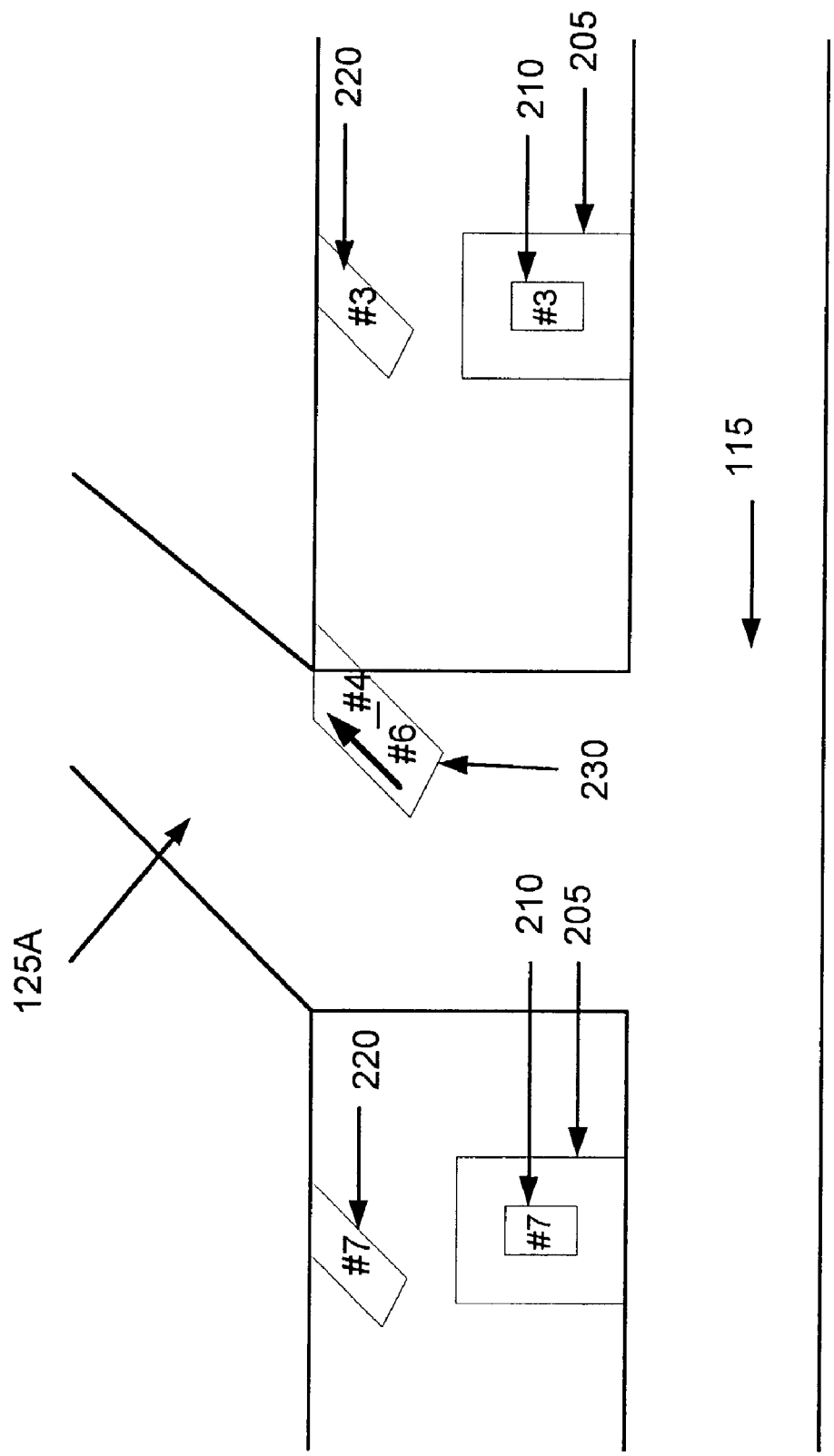
FIG. 2 is a top perspective view showing a portion of a main corridor and a short dead-end hallway that extends off the main corridor, with rooms and room numbers provided on the main corridor and the short hallway, in accordance with the first embodiment of the invention.

In the first embodiment, as shown in FIG. 2, each of the rooms 205 within the medical facility 100, including the rest rooms and storage areas, has a room number 210 prominently displayed on its door, starting with #1 (room closest to the entrance) and running sequentially from that number all the way to the room that is closest to the exit 130. The room numbers are also preferably provided on a sign 220 provided on the hallway wall directly above the door 205, whereby the sign 220 extends perpendicular from the hallway wall that the door of the room is located. That way, the sign 220 can be easily seen by someone walking along the hallway where the door is located. Preferably, both sides of the sign 220 are utilized, especially if the sign 220 is located on the main corridor 115.

For example, assuming that rooms #4, #5 and #6 are the only rooms accessible via a short dead-end hallway 125A, a sign 230 with "Rooms #4–#6" prominently displayed thereon is mounted on the wall of the main hallway at a junction where the short hallway 125A intersects with the main corridor 115. As a patient walks along the main corridor 115, the sign 230 is prominently positioned in the patient's line-of-sight. In the preferred embodiment, a directional arrow is also provided on the sign 230, to instruct the patient as to in which direction (left or right) to turn off the main corridor 115 in order to get to one of the rooms in the short hallway 125A.

In the first embodiment, there are preferably three rooms per each short dead-end hallway 125A to 125H, but of course one of ordinary skill in the art will recognize that any small number of rooms may be provided at each of the short dead-end hallways (with a possibility of having different numbers of rooms per each short dead-end hallway), while remaining within the scope of the invention as described herein. For example, a dead-end hallway may have one room, two rooms, four rooms, etc.

By way of example, referring back to FIG. 1, when a patient visits the medical facility to get treatment for a cold, the patient first goes to the counter 120 (as directed by one or more signs prominently displayed nearby the counter 120). A medical facility employee stationed at the counter 120 determines, based on information provided by way of a computer at the counter 120, whether or not any doctors and doctor rooms are available for this particular patient. If none is available, the patient is told to wait in a waiting room (e.g., room #1), whereby the patient may be notified, such as by a telecom system or by a hand-held buzzer device provided to the patient, to go back to the counter 120 to be given a room number to go to when a doctor becomes available to see the patient.

If a doctor and a doctor room are determined to be available when the patient first comes to the counter 120 (based on information as provided on a computer used by an employee manning the counter 120, such as by way of the system and method described in the '907 patent), the patient is provided with a room number to go to, and the patient is also provided with an electronic card so that the patient's location can be monitored while inside the medical facility 100.

Given the structure of the medical facility 100 with the single long corridor 115 with the short dead-end hallways 125A, 125B, . . . , 125H extending therefrom at 90 degree angles from the main corridor 115, the patient can easily navigate his or her way to the proper room, where a doctor is waiting to see the patient.

When the patient treatment is completed, the patient is told to walk down the main corridor 115 towards the exit 130. At the exit 130, a medical facility employee and/or a box is provided, so that the patient can remove the electronic card and return it to the medical facility 100, for reuse by another patient. In one implementation, the exit 130 is provided with sensors nearby (such as those used by department stores), which sense an electronic card's presence, and which provide a loud buzzer or other type of noise as a warning indication. When such a sound is heard, medical facility personnel who hear the warning indication will know that a patient has forgotten to return the electronic card. Accordingly, the patient can be interdicted before leaving the premises of the medical facility 100, so that the electronic card can be retrieved from the patient.

The present invention provides a basic and simple structure for a medical facility, to allow a patient to easily find their way within the facility. As such, it eliminates the time for facility personnel to have to give instructions to "lost" patients. It also saves a lot of confusion, and time spend lost. As such, appointment schedules can be met more readily, since patients will be less likely to miss their scheduled time for an appointment because they could not find their way to the proper room within the medical facility 100.

The present invention also saves time for patients, and saves money for the entity operating the medical facility 100, by lessening the amount of time employees have to spend in giving instructions to patients as to where to go to find a room within the medical facility 100. For patients who are not very conversant in English, the present invention provides a convenient way for those patients to make their way within the medical facility 100, without having to ask and re-ask someone who may not speak the same language as the patient, whereby hand signals sometimes are difficult to understand. The present invention overcomes this irksome problem.

Furthermore, the present invention lessens the stress on a patient, who no longer has to worry about finding his or her way through a medical facility "maze", while at the same time feeling sick. For example, patients who have children with them are typically stressed to begin with, not counting the stress caused by traffic that the patient had to deal with to get to the medical facility 100. By eliminating at least one source of stress, that being finding one's way within the medical facility 100, the present invention serves a useful purpose.

The present invention is also applicable to a multi-storied facility, whereby each separate story has a structure similar to that shown in FIG. 1, with a long main corridor and a large "entrance" counter provided at an entrance point to the long corridor. Once a person makes his or her way to the correct story of the building, such as by checking a sign at the lobby that directs the person to the correct story, then the person follows the same steps as described above for a one-story structure. For example, rooms in a first floor of the facility are provided with room numbers from 100 to 199, rooms in a second floor of the facility are provided with room numbers from 200 to 299, etc.

The present invention also provides a more efficient structure with respect to emergency evacuations, such as in the case of a fire. In the case of fire, fire exits have numbers and signs prominently displayed along the main corridor 115, whereby everyone within the medical facility 100 is directed to a proper Fire Escape exit and whereby everyone preferably exits the medical facility in a same direction along the main corridor 115. This lessens the problems associated with people panicking and going in opposite directions and running into each other when exiting the medical facility 100.

Also, communication within a facility is very simple with the present invention. For example, "Mary is in Room 21", "Jack is in Room 10". With these simple instructions, one can readily find Mary or Jack, by going to the room where they are currently located.

Furthermore, service personnel at the medical facility 100 can be easily directed to a proper location needing service. For example, "The electrical problem is in Room 12." With this information, a service person can quickly and efficiently make their way to the room needing servicing.

Therefore, in the present invention, regardless of what goes on in a room, it is just finding a number to get there, whereby the numbers are prominently displayed in the main corridor and/or in the short hallway in which the room can be entered.

In the preferred embodiment, referring now to FIG. 1, by way of example and not by way of limitation, there are 72 separate rooms in the medical facility 100. The breakdown of the 72 rooms is as follows, with label designations provided to show where these rooms are located in the preferred embodiment.

| Room Type | Number of Rooms |
| --- | --- |
| Doctor's office (20) | 5 |
| Nurses office (22) | 5 |
| Doctor/Patient room (24) | 15 |
| Minor Surgery room (26) | 5 |
| Physical Examination room (28) | 4 |
| X-Ray Room (30) | 1 |
| Dark Room (32) | 1 |
| Cast Setting Room (34) | 1 |
| Cast Supplies Room (36) | 1 |
| Laboratory Room (38) | 1 |
| Venipuncture Room (40) | 1 |
| Triage Room (42) | 1 |
| Communications Room (44) | 1 |
| Computer Room (46) | 1 |
| Check "In" and Waiting Room (48) | 1 |
| Coordinator Room "Out" (50) | 1 |
| Management Office (52) | 1 |
| Staff Lounge (54) | 1 |
| Waiting Room "Classes" (56) | 1 |
| Check Out and Waiting Room (58) | 1 |
| Group Therapy Room (60) | 1 |
| Media Room (62) | 1 |
| Rest Room (64) | 14 |
| Supply Room (66) | 3 |
| Locker Room "Staff" (68) | 1 |
| Entrance Vestibule (70) | 1 |
| Waiting Room Vestibule (72) | 1 |
| Telephone Room (74) | 1 |

Thus, a medical facility structure has been described according to several embodiments of the present invention. Many modifications and variations may be made to the techniques and structures described and illustrated herein without departing from the spirit and scope of the invention. Accordingly, it should be understood that the methods and apparatus described herein are illustrative only and are not limiting upon the scope of the invention. For example, one of ordinary skill in the art will recognize that a different number of rooms, and a different layout of rooms, and different types of rooms may be utilized instead of the specific number of rooms, layout of rooms, and types of rooms as shown in FIG. 1, while remaining within the spirit and scope of the invention.

What is claimed is:

1. A method for directing patients to proper locations within a medical facility, comprising:
   a) providing room number signs for each of a plurality of rooms within the medical facility, the medical facility including: i) a main corridor that extends in a substantially straight manner from an entrance to an exit of the medical facility, and ii) a plurality of hallways that extend substantially perpendicular off of the main corridor at different locations of the main corridor;
   b) sequentially numbering the rooms in the medical facility based on a relative location of each of the rooms with respect to the entrance;
   c) providing at least one sign adjacent to the entrance to the medical facility, which directs a patient to a counter;
   d) determining, based on real-time information as to locations of medical facility staff, whether or not the patient can be treated by one of the medical facility staff;
   e) if it is determined that the patient can be treated, providing the patient with an electronic card at the counter so as to monitor a current location of the patient, and directing the patient to a first particular room within the medical facility so that the patient can be treated; and
   f) directing the patient from the first particular room in which the patient has been treated, to a second particular room in which the patient will be treated next,
   wherein the step f) comprises:
      determining a room number of the second particular room in which the patient is to be treated, as compared to a room number of the first particular room in which the patient is currently located; and
      wherein the patient goes to the main corridor and travels in a first direction if the room number of the second particular room is higher than the room number of the first particular room, and the patient goes to the main corridor and travels in a second direction opposite the first direction if the room number of the second particular room is lower than the room number of the first particular room.

2. The method according to claim 1, further comprising: providing room numbers for each of the rooms within the medical facility, based on a position of the rooms with respect to the entrance, and displaying the room numbers on a sign adjacent each of the rooms.

3. The method according to claim 1, wherein, if the rooms are located along one of the at least two dead-end hallways, providing a sign at an intersection between the main corridor and the one of the at least two dead-end hallways, wherein the sign is positioned so as to be viewable by the patient as the patient walks along the main corridor.

4. The method according to claim 1, wherein, if it is determined that the patient cannot be treated immediately, directing the patient to a waiting area, to wait until the patient can be treated.

5. The method according to claim 4, wherein, if it is determined that the patient cannot be treated immediately, providing the patient with a notification device to notify the patient to go back to the counter at a later time when it is determined that the patient can be treated.

6. The method according to claim 1, wherein the main corridor spans an entire length of the medical facility.

7. The method according to claim 6, wherein all of the rooms in the medical facility are provided with a corresponding room number.

8. The method according to claim 1, wherein each of the plurality of hallways is a dead-end hallway.

9. A method for directing a patient to a treatment room within a medical facility, comprising:
   a) providing room numbers for each of a plurality of rooms within the medical facility starting with a room closest to an entrance of the medical facility, in such a manner that the room numbers either sequentially increase or decrease to thereby signify a relative location of each respective one of the rooms with respect to the entrance, an exit of the medical facility, and each of the other rooms in the medical facility, wherein the medical facility includes: i) a main corridor that extends in a substantially straight manner from the entrance to the exit of the medical facility, and ii) a plurality of hallways that extend substantially perpendicular from the main corridor at different locations off the main corridor;
   b) providing all patients in the medical facility and all medical staff within the medical facility with electronic cards that are used to determine a particular location of each of the patients and each of the medical staff within the medical facility at any particular moment in time;
   c) providing all of the rooms within the medical facility with card receiving devices that are capable of reading electronic card information to thereby provide information to a specific site in the medical facility with regards to which persons, if any, are currently located in each of the rooms of the medical facility;
   d) providing a plurality of room number range signs on a wall of the main corridor adjacent to each of the plurality of hallways, wherein each of the room number range signs includes a room number range for all rooms that are directly accessible by way of the corresponding one of the hallways that is adjacent to the corresponding one of the room number range signs;
   e) receiving a patient in a receiving area located adjacent to the entrance of the medical facility, and providing the patient with an electronic card to be carried by the patient at all times within the medical facility;
   f) based on the information obtained in step d), determining if any of the rooms in the medical facility is available to provide a particular treatment required for the patient, and if one of the rooms is available, directing the patient to go to the one of rooms in the medical facility and providing the patient with the corresponding room number of the one of the rooms,
   wherein the patient is able to travel from the receiving area to the one of the rooms based solely on the corresponding room number of the one of the rooms provided to the patient in step f) and the room number range signs provided on the wall of the main corridor that the patient views when traveling along the main corridor to determine which of the room number range signs has a room number range that includes the corresponding room number that the patient is traveling to.

10. The method according to claim 9, wherein the main corridor spans an entire length of the medical facility.

11. The method according to claim 10, wherein all of the rooms in the medical facility are provided with a corresponding room number.

12. The method according to claim 9, wherein each of the plurality of hallways is a dead-end hallway.

* * * * *